United States Patent [19]

Yoshimura et al.

[11] Patent Number: 6,049,016

[45] Date of Patent: Apr. 11, 2000

[54] PROCESS FOR PRODUCING PENTAFLUOROETHANE AND TETRAFLUOROCHLOROETHANE

[75] Inventors: Toshikazu Yoshimura; Yukio Homoto; Yasufu Yamada; Takehide Tsuda; Takashi Shibanuma, all of Osaka, Japan

[73] Assignee: Daikin Industries Ltd., Osaka, Japan

[21] Appl. No.: 09/359,644

[22] Filed: Jul. 26, 1999

Related U.S. Application Data

[62] Division of application No. 08/894,472, filed as application No. PCT/JP96/00401, Feb. 22, 1996.

[30] Foreign Application Priority Data

Feb. 24, 1995 [JP] Japan ........................................ 7-36793

[51] Int. Cl.[7] .................................................. C07C 17/08
[52] U.S. Cl. ............................ 570/169; 570/167; 570/168
[58] Field of Search ..................................... 570/169, 167, 570/168

[56] References Cited

U.S. PATENT DOCUMENTS 4,258,225  3/1981  Feiring .
4,911,792  3/1990  Manzer et al. .

FOREIGN PATENT DOCUMENTS

| 514932A2 | 11/1992 | European Pat. Off. . |
| 353970B1 | 3/1993 | European Pat. Off. . |
| 2167803 | 6/1990 | Japan . |
| 5146680 | 6/1993 | Japan . |
| WO 9216479 | 10/1992 | WIPO . |
| WO 9216482 | 10/1992 | WIPO . |

*Primary Examiner*—Alan Siegel
*Attorney, Agent, or Firm*—Birch, Stewart, Kolasch & Birch, LLP

[57] ABSTRACT

There is provided a process for producing HFC-125 and/or HCFC-124 from PCE, characterized by the first reaction step of fluorinating PCE in the presence of catalyst in a liquid phase to form HCFC-123 and/or HCFC-122 and the second reaction step of fluorinating HCFC-123 and/or HCFC-122 in the presence of catalyst in a vapor phase to form HFC-125 and/or HCFC-124.

This process is improved in the yield of objective products, and life of catalyst, and the controllability of reaction temperature.

6 Claims, 3 Drawing Sheets

PROCESS FOR PRODUCING PENTAFLUOROETHANE AND TETRAFLUOROCHLOROETHANE

This application is divisional of co-pending application Ser. No. 08/894,472, filed on Aug. 20, 1997. Application Ser. No. 08/894,472 is the national phase of PCT International Application No. PCT/JP96/00401 filed on Feb. 22, 1996 under 35 U.S.C. §371. The entire contents of each of the above-identified applications are hereby incorporated by reference.

TECHNICAL FIELD

The present invention relates to a process of producing pentafluoroethane (which is hereinafter also referred to as. "HFC-125") which is useful as an alternative flon compound without chlorine and which is used as a refrigerant, and a process of producing 1,1,1,2-tetrafluorochloroethane (which is hereinafter also referred to as "HCFC-124") which is useful as an alternative flon and a starting material for an alternative flon.

BACKGROUND ART

As a process of producing HCFC-124 and HFC-125, a process has been known in which perchloroethylene (which is hereinafter also referred to as "PCE") is reacted with an excessive amount of hydrogen fluoride (which is hereinafter also referred to as "HF") in a vapor phase to form 1, 1-dichloro-2,2, 2-trifluoroethane (which is hereinafter also referred to as "HCFC-123"), HCFC-124 and HFC-125 (see International Publication No. WO 92/16479). The Publication discloses that HCFC-123, HCFC-124 and HCFC-125 are formed at a HF/PCE molar ratio between about 3/1 and 10/1, a reaction. temperature between 250° C. and 450° C., and a reaction contact period between 0.1 sec. and 60 sec. using a metal such as zinc and/or chromium supported on alumina and/or aluminum fluoride as vapor phase reaction catalyst.

The inventors have found that when such a process is carried out, the following problems occur due to a large amount of generated reaction heat: difficult reaction control, remarkable degradation of catalyst performance, and formation of a relatively large amount of by-products. The reaction which produces HFC-125 by reacting PCE and HF is an exothermic reaction of which heat of reaction is so large as about 28 kcal/mol. Thus, when the reaction is carried out in a vapor phase, a hot spot is formed in a reactor so that reaction temperature control may become difficult, and a large amount of by-products may be sometimes formed due to the temperature increase, which reduces a yield of an objective product. One manner which overcomes these problems uses a multi-tubular reactor for the reactor. However, this manner requires an expensive facilities cost, which becomes another problem. Another manner overcoming the problems increases a large molar ratio of HF/PCE and uses unreacted PCE as a diluent so as to stably control the temperature. In this manner, an amount of a starting material stream which flows through the reaction process is increased, so that a scale of a reaction facilities becomes large, which is also another problem.

Thus, it has been desired to provide a process which overcomes the above problems and which effectively produces HFC-125 and/or HCFC-124 in a commercial scale at an inexpensive cost.

It is to be noted that the above International Publication discloses only the vapor phase reaction as described above, and does not disclose the catalyst degradation, a manner of prevention of the catalyst degradation, a control manner of generated reaction heat, a separation process of reaction mixture comprising products and by-products, recirculation of unreacted HF, or recirculation of HCFC-123, HCFC-124 and so on for purpose of the production of HFC-125, which is explained in the detail below in the present description.

Although each of a process for the production of HCFC-123 through a liquid phase reaction using PCE as a starting material, and a process for the production of HCFC-124 and/or HFC-125 through a vapor phase reaction using HCFC-123 as a starting material is known individually as explained below, no profit obtained by combining these process has been known, and the profit is firstly provided by the present invention.

As a production process of 1,1,2-trichloro-2,2-difluoroethane (which is hereinafter also referred to as "HCFC-122") and HCFC-123, a process has been known in which PCE and HF are reacted in a liquid phase to form 1, 1,2,2-tetrachlorofluoroethane (which is hereinafter also referred to as "HCFC-121"), HCFC-122 and HCFC-123 (see U.S. Pat. No. 4,258,225). The patent discloses tantalum fluoride ($TaF_5$) or niobium fluoride ($NbF_5$) as catalyst used in the liquid phase reaction. As in the case of the above International Publication, a withdrawal process of reaction products from the reaction process, a separation process of the reaction mixture, a recirculating process of the reaction mixture or the like, which is disclosed by the present description.

A process for the production of HCFC-124 and HFC-125 from HCFC-123 as a starting material has been known in which HCFC-124 and HFC-125 are formed by reacting HCFC-123 with an excessive amount of HF in a vapor phase (see International Publication No. WO 92/16482). The Publication discloses that HCFC-124 and HCFC-125 are formed at a HF/HCFC-123 molar ratio between about 2/1 and 10/1, a reaction temperature between 225° C. and 450° C., and a reaction contact period between 0.1 sec. and 60 sec. using a metal such as zinc and/or chromium supported on alumina and/or aluminum fluoride as vapor phase reaction catalyst. As in the case of the above International Publication, this Publication does not disclose a separation process of the reaction mixture comprising the products and the by-products or recirculation of unreacted HF, HCFC-123 and so on, which is disclosed by the present description. In addition, no production process is disclosed which produces HCFC-123 as a starting material.

By the way, as to separation of HF and organic materials relating to the present invention from a mixture comprising those materials, for example a process has been known in which a mixture of HCFC-123, HCFC-124 and HF is cooled to cause liquid phase separation (i.e. separation into insoluble liquid phases) so that the mixture is separated into a liquid phase which is composed mainly of HF and another liquid phase which is composed mainly of HCFC-123 and HCFC-124 (see European Patent Publication (EP-B) No. 353970). The Publication discloses further separation of each of HF, HCFC-123 and HCFC-124 by means of distillation after the liquid phase separation.

OBJECTS OF THE INVENTION

It is an object of the present invention to provide a process of producing HFC-125 and/or HCFC-124 which overcomes the problems as described above upon the production of those compounds and which produces those compounds effectively in a commercial scale at a low cost.

DISCLOSES OF THE INVENTION

The present inventors have found that a production process of HFC-125 and/or HCFC-124 comprising the steps of fluorinating PCE in the presence of catalyst in a liquid phase first reaction step to produce HCFC-123 and/or HCFC-122, and then fluorinating said HCFC-123 and/or HCFC-122 in the presence of catalyst in a vapor phase second reaction step to produce HFC-125 and/or HCFC-124 is effective for the extension of catalyst lives, and able to economically and effectively produce HFC-125 and/or HCFC-124 in a commercial scale, which leads to the present invention.

Thus, the present invention provides, in the first aspect, a process of producing HFC-125 comprising the steps of:
- (1-a) reacting PCE and HF in the presence of catalyst at a reaction temperature in the range between 60° C. and 150° C. in a liquid phase first reaction step so as to obtain HCFC-123 and/or HCFC-122,
- (1-b) reacting HF and HCFC-123 and/or HCFC-122 obtained in the step (1-a) in the presence of catalyst at a reaction temperature between 250° C. and 450° C. in a vapor phase second reaction step so as to obtain a reaction mixture comprising HFC-125, and
- (1-c) separating out HFC-125 from the reaction mixture obtained in the step (1-b).

In a first preferable embodiment of the first aspect, the present invention provides a process of producing HFC-125 comprising the steps of:
- (1-i-a) reacting PCE and HF in the presence of catalyst at a reaction temperature in the range between 60° C. and 150° C. in a liquid phase first reaction step so as to obtain a first reaction mixture comprising HCFC-123 and/or HCFC-122,
- (1-i-b) obtaining a first fraction from the first reaction mixture which fraction comprises HCFC-123 and/or HCFC-122 and hydrogen chloride (which is hereinafter also referred to as "HCl") and a portion of unreacted HF,
- (1-i-c) reacting the first fraction, optionally with additional HF, in the presence of catalyst at a reaction temperature in the range between 250° C. and 450° C. in a vapor phase second reaction step so as to obtain a second reaction mixture comprising HCFC-123, HCFC-124, HFC-125, HCl and HF,
- (1-i-d) separating the second reaction mixture into three fractions: a second fraction which comprises most of HCFC-123 and/or HCFC-124 of the second reaction mixture and HF entrained therewith, a third fraction which comprises most of HFC-125 and HCl of the second reaction mixture, and a fourth fraction which comprises the rest of HF,
- (1-i-e) recirculating (or returning or recycling) the second fraction to the step (1-i-c) and reacting it together there,
- (1-i-f) recirculating the fourth fraction to the step (1-i-a) and/or the step (1-i-c) and reacting it together there, and
- (1-i-g) separating out HFC-125 from the third fraction.

In the step (1-i-b) of the above first embodiment, the first fraction may be obtained by removing most of PCE and preferably substantially all of PCE from the first reaction mixture. In this removal, unreacted HF is entrained with the removed PCE, and thus removed PCE and entrained HF are preferably recirculated to the liquid phase first reaction step. The features of this paragraph are also applicable to a corresponding step of other embodiments described below.

In the present description, the term "substantially all" is intended not to mean strict "all" (i.e. 100%), and the term is to be interpreted within an industrially feasible range based on an extent those skilled in the art can expect. Usually, "substantially all" may be interpreted to mean at least 90%, preferably at least 95% and for example at least 99% or more of a component contained in a mixture in question.

In the present description, the term "most" is intend be interpreted to include "substantially all" and an amount less than "substantially all". Usually, "most" may be interpreted to mean at least 50%, preferably at least 70%, more preferably at least 90% and for example at least 95% or more of a component contained in a mixture in question.

It is noted that concrete figures of the terms "substantially all" and "most" can be easily determined by those skilled in the art considering various factors of a process such as an operating cost, a fixed cost and so on.

In a second preferable embodiment of the first aspect, the present invention provides a process of producing HFC-125 comprising the steps of:
- (1-ii-a) reacting PCE and HF in the presence of catalyst at a reaction temperature in the range between 60° C. and 150° C. in a liquid phase first reaction step so as to obtain a first reaction mixture comprising HCFC-123 and/or HCFC-122,
- (1-ii-b) obtaining a first fraction from the first reaction mixture which fraction comprises HCFC-123 and/or HCFC-122 and HCl and a portion of unreacted HF,
- (1-ii-c) obtaining a fifth fraction by removing at least a portion, preferably at least 95%, for example 98% and more preferably substantially all of HCl from the first fraction,
- (1-ii-d) reacting the fifth fraction, optionally with additional HF, in the presence of catalyst at a reaction temperature in the range between 250° C. and 450° C. in a vapor phase second reaction step so as to obtain a second reaction mixture comprising HCFC-123, HCFC-124, HFC-125, HCl and HF,
- (1-ii-e) separating the second reaction mixture into three fractions: a second fraction which comprises most of HCFC-123 and/or HCFC-124 of the second reaction mixture and HF entrained therewith, a third fraction which comprises most of HFC-125 and HCl of the second reaction mixture, and a fourth fraction which comprises the rest of HF,
- (1-ii-f) recirculating the second fraction to the step (1-ii-d) and reacting it together there,
- (1-ii-g) recirculating the fourth fraction to the step (1-ii-a) and/or the step (1-ii-d) and reacting it together there, and
- (1-ii-h) separating out HFC-125 from the third fraction.

In a third preferable embodiment of the first aspect, the present invention provides a process of producing HFC-125 comprising the steps of:
- (1-iii-a) reacting PCE and HF in the presence of catalyst at a reaction temperature in the range between 60° C. and 150° C. in a liquid phase first reaction step so as to obtain a first reaction mixture comprising HCFC-123 and/or HCFC-122,
- (1-iii-b) obtaining a first fraction from the first reaction mixture which fraction comprises HCFC-123 and/or HCFC-122 and HCl and a portion of unreacted HF,
- (1-iii-c) obtaining a fifth fraction by removing at least a portion, preferably at least 95%, for example 98% and more preferably substantially all of HCl from the first fraction,
- (1-iii-d) reacting the fifth fraction, optionally with additional HF, in the presence of catalyst at a reaction temperature in the range between 250° C. and 450° C. in a vapor phase second reaction step so as to obtain a second reaction mixture comprising HCFC-123, HCFC-124, HFC-125, HCl and HF, (1-iii-e) recirculating the second reaction mixture to the step (1-iii-c) and separating the second reaction mixture and the first fraction into three fractions: a second fraction which comprises most of HCFC-123 and/or HCFC-124 of the second reaction mixture and the first fraction, and HF entrained therewith which second fraction replaces the fifth fraction, a third fraction which comprises most of HFC-125 and HCl of the second reaction mixture and the first fraction, and a fourth fraction which comprises the rest of HF, (1-iii-f) reacting the second fraction in place of the fifth fraction in the step (1-iii-d), (1-iii-g) recirculating the fourth fraction to the liquid phase first reaction step and/or the vapor phase second reaction step and reacting it together there, and (1-iii-h) separating out HFC-125 from the third fraction.

The present invention provides, in the second aspect, a process of producing HCFC-124 comprising the steps of:

(2-a) reacting PCE and HF in the presence of catalyst at a reaction temperature in the range between 60° C. and 150° C. in a liquid phase first reaction step so as to obtain HCFC-123 and/or HCFC-122, (2-b) reacting HF and HCFC-123 and/or HCFC-122 obtained in the step (2-a) in the presence of catalyst at a reaction temperature in the range between 200° C. and 450° C. in a vapor phase second reaction step so as to obtain a reaction mixture comprising HCFC-124, and (2-c) separating out HFC-125 from the reaction mixture obtained in the step (2-b).

In a first preferable embodiment of the second aspect, the present invention provides a process of producing HCFC-124 comprising the steps of:

(2-i-a) reacting PCE and HF in the presence of catalyst at a reaction temperature in the range between 60° C. and 150° C. in a liquid phase first reaction step so as to obtain a first reaction mixture comprising HCFC-123 and/or HCFC-122, (2-i-b) obtaining a first fraction from the first reaction mixture which fraction comprises HCFC-123 and/or HCFC-122 and HCl and a portion of unreacted HF, (2-i-c) reacting the first fraction, optionally with additional HF, in the presence of catalyst at a reaction temperature in the range between 200° C. and 450° C. in a vapor phase second reaction step so as to obtain a second reaction mixture comprising HCFC-123, HCFC-124, HCl and HF, (2-i-d) separating the second reaction mixture into three fractions: a second fraction which comprises most of HCFC-123 of the second reaction mixture and HF entrained therewith, a third fraction which comprises most of HCFC-124 and HCl of the second reaction mixture, and a fourth fraction which comprises the rest of HF, (2-i-e) recirculating the second fraction to the step (2-i-c) and reacting it together there, (2-i-f) recirculating the fourth fraction to the step (2-i-a) and/or the step (2-i-c) and reacting it together there, and (2-i-g) separating out HCFC-124 from the third fraction.

In a second preferable embodiment of the second aspect, the present invention provides a process of producing HCFC-124 comprising the steps of:

(2-ii-a) reacting PCE and HF in the presence of catalyst at a reaction temperature in the range between 60° C. and 150° C. in a liquid phase first reaction step so as to obtain a first reaction mixture comprising HCFC-123 and/or HCFC-122, (2-ii-b) obtaining a first fraction from the first reaction mixture which fraction comprises HCFC-123 and/or HCFC-122 and HCl and a portion of unreacted HF, (2-ii-c) obtaining a fifth fraction by removing at least a portion, preferably at least 95%, for example 98% and more preferably substantially all of HCl from the first fraction, (2-ii-d) reacting the fifth fraction, optionally with additional HF, in the presence of catalyst at a reaction temperature in the range between 200° C. and 450° C. in a vapor phase second reaction step so as to obtain a second reaction mixture comprising HCFC-123, HCFC-124, HCl and HF, (2-ii-e) separating the second reaction mixture into three fraction: a second fraction which comprises most of HCFC-123 of the second reaction mixture and HF entrained therewith, a third fraction which comprises most of HCFC-124 and HCl of the second reaction mixture, and a fourth fraction which comprises the rest of HF, (2-ii-f) recirculating the second fraction to the step (2-ii-d) and reacting it together there, (2-ii-g) recirculating the fourth fraction to the step (2-ii-a) and/or the step (2-ii-d) and reacting it together there, and (2-ii-h) separating out, HCFC-124 from the third fraction.

In a third preferable embodiment of the second aspect, the present invention provides a process of producing HCFC-124 comprising the steps of:

(2-iii-a) reacting PCE and HF in the presence of catalyst at a reaction temperature in the range between 60° C. and 150° C. in a liquid phase first reaction step so as to obtain a first reaction mixture comprising HCFC-123 and/or HCFC-122, (2-iii-b) obtaining a first fraction from the first reaction mixture which fraction comprises HCFC-123 and/or HCFC-122 and HCl and a portion of unreacted HF, (2-iii-c) obtaining a fifth fraction by removing at least a portion, preferably at least 95%, for example 98% and more preferably substantially all of HCl from the first fraction, (2-iii-d) reacting the fifth fraction, optionally with additional HF, in the presence of catalyst at a reaction temperature in the range between 200° C. and 450° C. in a vapor phase second reaction step so as to obtain a second reaction mixture comprising HCFC-123, HCFC-124, HCl and HF, (2-iii-e) recirculating the second reaction mixture to the step (2-iii-c) and separating the second reaction mixture and the first fraction into three fractions: a second fraction which comprises most of HCFC-123 of the second reaction mixture and the first fraction, and HF entrained therewith which second fraction replaces the fifth fraction, a third fraction which comprises most of HCFC-124 and HCl of the second reaction mixture and the first fraction, and a fourth fraction which comprises the rest of HF, (2-iii-f) reacting the second fraction in place of the fifth fraction in the step (2-iii-d), (2-iii-g) recirculating the fourth fraction to the liquid phase first reaction step and/or the vapor phase second reaction step and reacting it together there, and (2-iii-h) separating out HCFC-124 from the third fraction.

Any of the processes of the present invention can be carried out in a batch process or a continuous process, but the continuous process is effectively carried out in a commercial scale. In such a case, PCE and HF may be continuously supplied to the liquid phase first reaction step while each of the steps such as the vapor phases second reaction step, the separation step, the recirculating step and so on may be continuously carried out. Those skilled in the art can easily select details for the continuous operation like this on the basis of the concept of the present invention (i.e. the combination of the vapor phase first reaction step and the liquid phase second reaction step) and its detailed description as described above and below considering the objective product and practical limitations and so on (for example, factors concerning product qualities, utilities and so on).

Figure 1:
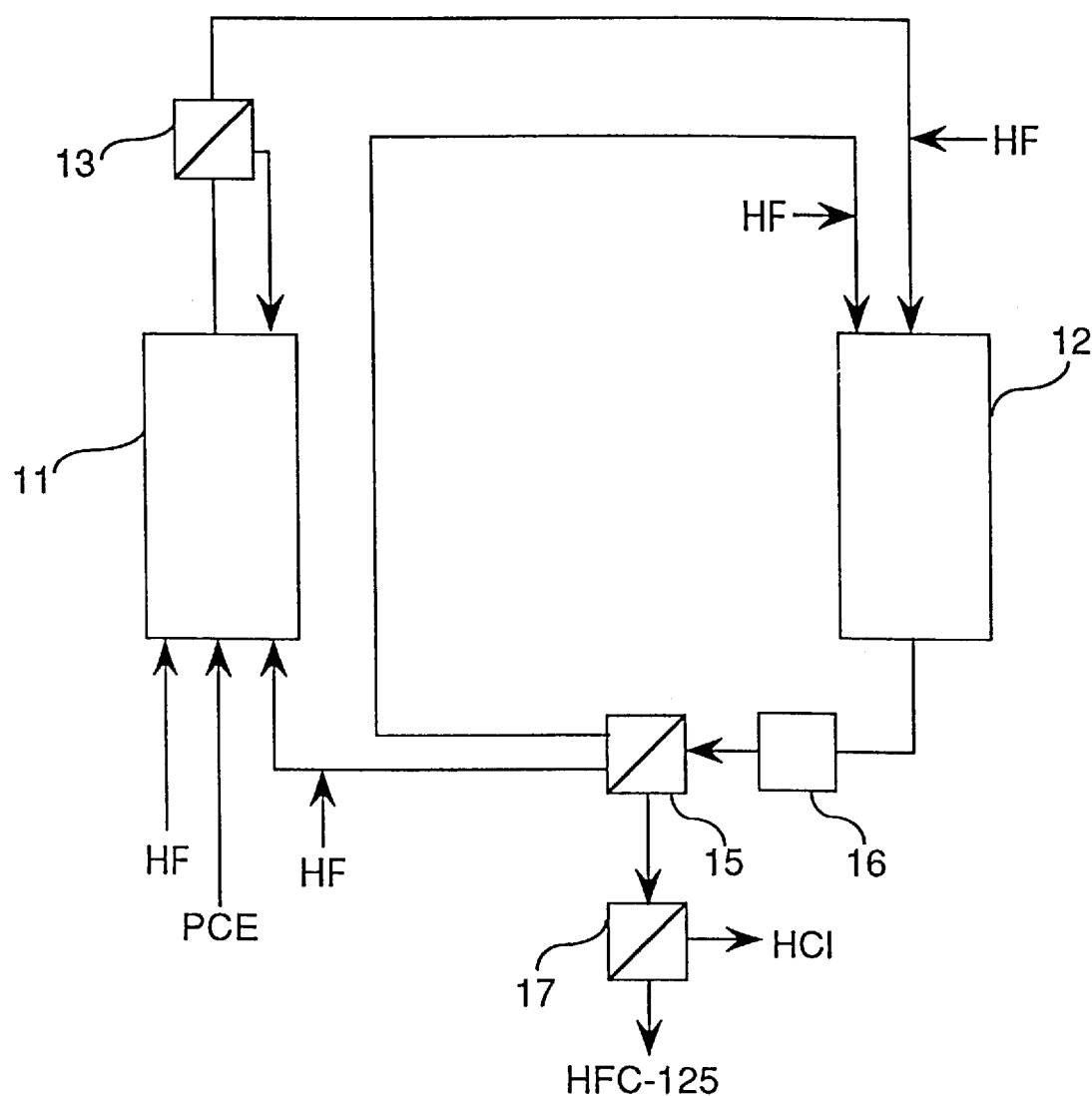
FIG. 1 is a process flow sheet which schematically shows a process of the first preferable embodiment of the first or the second aspect of the present invention.

In the drawings, the references indicate as follows:

11, 21 and 31: liquid phase first reaction step;

12, 22 and 32: vapor phase second reaction step;

13, 15, 17, 23, 24, 25, 28, 33, 34 and 38: separation step (for example a step using a distillation column); and

26, 27, 36 and 37: pressure increasing step (for example a step using a booster).

DETAILED DESCRIPTION OF THE INVENTION

The present process can be expressed using the following reaction formulas:

In the liquid phase first reaction step, PCE which is supplied with HF is fluorinated according to the following formulas (1) and (2), and HCFC-123 and/or HCFC-122 and HCl are formed:

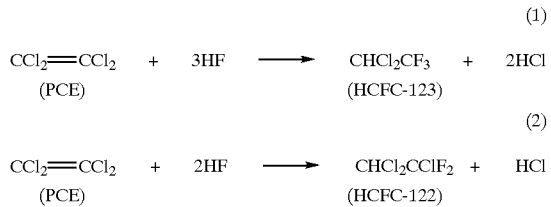

The above reactions proceed in a liquid phase reactor. The first reaction mixture withdrawn from the reactor is supplied to the vapor phase second reaction step, preferably after removing unreacted PCE and a portion of HF. Said portion of the unreacted HF is HF which is entrained with the unreacted PCE when the unreacted PCE is removed.

Reactions of HCFC-123 and/or HCFC-122 and HF which are supplied to the vapor phase second reaction step are successive reactions expressed by the following reaction formulas (3) and (4) in which HCFC-124 is formed, and by the following reaction formula (5) in which the formed HCFC-124 is fluorinated to form HFC-125:

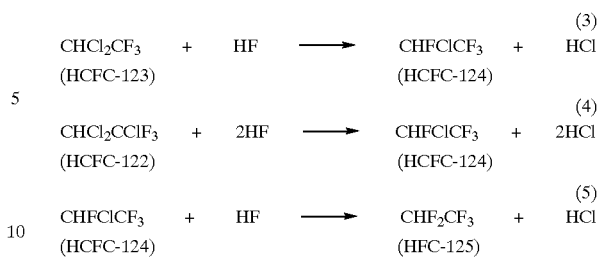

The reaction (3), (4) and (5) are equilibrium reactions, respectively. Thus, when HCl produced in the liquid phase first reaction step is supplied to the vapor phase second reaction step together with HCFC-123 and/or HCFC-122 and HF, it is difficult for reactions (3), (4) and (5) to proceed toward the production of HCFC-124 and HFC-125.

Therefore, it is preferable that PCE and a portion of HF is removed from the produced first reaction mixture and then HCl is further removed therefrom so as to obtain HCFC-123 and/or HCFC-122 and HF, which are supplied to the vapor phase second reaction step (for example, in the second and the third embodiments, HCl is removed before the vapor phase second reaction step). In such a case, there may be a preferable situation in which a concentration of HF is higher depending on reaction conditions of the vapor phase reaction step, and thus HF from the first reaction mixture alone which is entrained with HCFC-123 and/or HCFC-122 may be insufficient for such a higher concentration. In such a case, additional HF may be supplied from the outside.

In the present invention, the reactions (1) and (2) are liquid phase reactions, and the reactions (3), (4) and (5) are vapor phase reactions. In the present invention, a conventional liquid phase reactor, for example a stirred tank reactor in which catalyst is suspended may be used for the liquid phase reactions. By properly selecting a temperature and a pressure of the reaction system, the reaction system may be operated in the liquid phase. Similarly to the liquid phase reaction, a conventional vapor phase reactor, for example a tubular reactor which is filled with catalyst may be used for the vapor phase reaction in the present invention, and by properly selecting a temperature and a pressure of the reaction system, the reaction system may be operated in the vapor phase. For the vapor phase reaction, also an adiabatic reactor may be used.

When PCE is fluorinated in the liquid phase first reaction step, generally the reaction temperature is in the range between 60° C. and 150° C. and preferably between 80° C. and 120° C., and the reaction pressure is in the range between 0.1 MPa and 3.0 MPa (absolute pressure) and preferably between 0.6 MPa and 1.6 MPa (absolute pressure).

The reaction time (or average residence time) of the liquid phase first reaction step is usually in the range between 0.1 hr to 10 hrs. and preferably between 0.5 hrs and 2 hrs. An amount of HF newly supplied per 1 mol of PCE may be an about stoichiometric amount of HF (i.e. an amount theoretically necessary to obtain an objective product) or more (for example in the range between about 1 mol and 5 mol) provided that HF is not supplied in any other point. The feed material to the liquid phase reaction step may contain, in addition to the newly supplied HF and PCE, recirculated HF which is recovered in the vapor phase second reaction step. The compounds such as HCFC-123, HFC-125, HCFC-124 and/or HCl and so on which may be entrained with the recirculated HF may be also supplied to the liquid phase first reaction step.

As the fluorination catalyst used in liquid phase first reaction step, for example antimony fluoride, titanium fluoride, tin fluoride, antimony fluoride chloride, titanium fluoride chloride, tin fluoride chloride and so on may be used. Among them, antimony fluoride chloride of $SbCl_xF_y$ (wherein x+y=5 and $3 \leq y \leq 5$) is preferable, and such antimony fluoride chloride in which y is in the range between 4 and 5 is in particular preferable. When y is less than 3, formation of undesirable by-products is likely to increase. Such by-products are for example tetrachlorodifluoroethane trichlorotrifluoroethane and so on except HCFC-123 and/or HCFC-122.

The step in which a portion (i.e. the unreacted PCE and a portion of unreacted HF) is removed from the first reaction mixture withdrawn from the liquid phase reactor and the balance is obtained as the first fraction as described above may be carried out by conducting the reaction under a reflux condition in a liquid phase reactor equipped with a reflux condenser and taking out a gas mixture evaporating from the reaction system as condensed liquid or by partially condensing the gas mixture and taking out the remaining as non-condensed gas. Since the boiling point of PCE is considerably lower than that of HCFC-123, HCFC-122 or HCl, it is generally possible to easily separate PCE from the first reaction mixture containing PCE and recirculate the separated PCE to the liquid phase first reaction step. If the separation of PCE is insufficient, a separation step (such as distillation) may be further added.

It is noted that the following separation has been already known to be feasible: The first reaction mixture from the liquid phase reaction step is separated into a fraction comprising HCFC-123 and/or HCFC-122 and a fraction comprising HF by combining liquid phase separation (i.e. separation into liquid phases which are insoluble with each other) and distillation operations. However, since it is known that HF of the first reaction mixture may be used for the fluorination of the vapor phase second reaction step (thus, it is not necessary to separate HF from HCFC-123 and/or HCFC-122), and that HCFC-123 and HF, and HCFC-122 and HF form azeotropic mixtures, respectively, it is possible to take out HCFC-123, HCFC-122 and HF at a constant ratio of (HCFC-123 and HCFC-122)/HF by using a liquid phase reactor which includes a distillation column and a reflux condenser on the reactor. In fact, the first reaction mixture includes also unreacted PCE and HCl. The first reaction mixture may be subjected to a distillation step and the azeotropic mixtures may be taken out as side cut streams, and the mixtures may be used in the vapor phase second reaction step as starting feed materials. The azeotropic composition (a molar ratio) of HCFC-123 and HF is about 1:2.6 (at a pressure of 0.24 MPa-abs., an azeotropic point of 40° C.), and the azeotropic composition (a molar ratio) of HCFC-122 and HF is about 1:4 (at a pressure of 0.2 MPa-abs., an azeotropic point of 47° C.). As to the azeotrope, Japanese Patent Kokai Publication (JP-A) No. 90-167803 may be referred to, which discloses the azeotrope of HCFC-123 and HF. The disclosure of the Publication constitutes a portion of the present description by the reference. It is of course possible to take out a fraction comprising the azeotropic mixtures and HCl (which corresponds to the first fraction) in a first distillation step (namely, to remove at least PCE), and then to separate into a fraction comprising HCl and a fraction comprising the azeotropic mixtures in a subsequent distillation step.

The first fraction taken out includes HCl, HCFC-123 and/or HCFC-122 and a portion of unreacted HF, and unreacted PCE may be included depending on an extent of the separation. When the unreacted PCE is included, as described above, a distillation column is placed directly on the reactor or separately placed downstream of the liquid phase first reaction step so that PCE is separated and recirculated to the liquid phase first reaction step. This separation can be easily carried out since the boiling point of PCE is higher than those of other reaction products. As seen, the process of the present invention is characterized in that the mixture which does not contain PCE is supplied to the vapor phase second reaction step.

In the second preferable embodiments of the first and the second aspects (and in the step (c) of the third preferable embodiments of those aspects), the first fraction obtained from the reaction mixture of the liquid phase reactor is separated into a fraction comprising substantially all HCl of the first fraction and a fraction comprising the remaining HCFC-123 and/or HCFC-122 and HF (i.e. the fifth fraction) under consideration of the equilibriums of the vapor phase reaction step. This separation may be carried out any appropriate separation step, and in a preferable embodiment, a distillation step can easily carry out the separation considering that HCl has a lower boiling point than those of the others.

In the third preferable embodiment (step (e)) of the first aspect, the second reaction mixture produced in the vapor phase second reaction step and the first fraction is divided into the third fraction comprising most of HFC-125 and HCl, the fifth fraction comprising most of HCFC-122, HCFC-123 and HCFC-124 and HF which is entrained (and preferably azeotropically distilled) with those HCFCs, and the fourth fraction comprising the rest of HF.

In the third preferable embodiment (step (e)) of the second aspect, the second reaction mixture produced in the vapor phase second reaction step and the first fraction is divided into the third fraction comprising most of HCFC-124 and HCl, the fifth fraction comprising most of HCFC-122 and HCFC-123 and HF which is entrained (and preferably azeotropically distilled) with those HCFCs, and the fourth fraction comprising the rest of HF.

In any embodiment, the fractions may be obtained by any appropriate separation process, for example, a distillation process. When the distillation process is used, these three fractions may be obtained with a single distillation step. That is, it is possible to withdraw, in the order of a low boiling point, the third fraction from the top of a distillation column, the fifth fraction from an intermediate tray below a feed tray of the distillation column, and the fourth fraction from the bottom of the distillation column.

One of the important features of the present invention is in that substantially all of PCE is removed from the reaction mixture of the liquid phase reaction step so that the first fraction which contains HF is taken out, and such first fraction is supplied to the vapor phase second reaction step. This is based on a find by the present inventors in that if PCE is present in the vapor reaction of the second reaction step, an amount of generated heat is highly increased that the reaction temperature control becomes difficult, whereby the catalyst is degraded.

One of the features of the preferable embodiments of the present invention is in that substantially all of PCE is removed from the reaction mixture of the liquid phase reaction step so that the reaction mixture still contains HF, HCl is removed from thus reaction mixture containing HF (which mixture corresponds to the first reaction mixture), and the reaction mixture is supplied to the vapor phase reaction step after the removal of HCl. When HCl is present upon the vapor phase reaction, yields of HFC-125 and HCFC-124 are undesirably decreased as described above.

In the present invention, since the vapor phase reaction step may be carried out at a relatively low molar ratio of HF based on HCFC-123 and/or HCFC-122 (HF: HCFC-123 and/or HCFC-122), the reaction mixture withdrawn from the liquid phase reaction step may be used in the vapor phase reaction step as it is after the removal of PCE and optionally HCl. For example, an amount of HF may be once to five times of the stoichiometric amount of HF (i.e. an HF amount which is theoretically necessary to obtain an objective product (such as HCFC-124 and/or HFC-125) from a starting material (such as HCFC-123 and/or HCFC-122)). It is of course possible that an amount of HF is more than such an amount. Thus, any complicated facilities may be omitted which are required to separate HCFC-123 and/or HCFC-122 by means the liquid phase separation, the distillation and so on.

In the second reaction step of the present invention in which HCFC-123 and/or HCFC-122 are fluorinated in the vapor phase by means of HF, the reaction temperature is in the range usually between 250° C. and 450° C. and preferably between 290° C. and 400° C. when HFC-125 is formed.

When the reaction temperature is lower than 250° C., an amount of produced HFC-125 is reduced, and when the reaction temperature is higher than 450° C., amounts of the produced by-products increase. The reaction pressure is in the range usually between 0.1 MPa and 2.0 MPa (absolute pressure) and preferably between 0.1 MPa and 0.5 MPa (absolute pressure). As to the conditions for the production of HCFC-124, they may be similar to those for the production of HFC-125 except that the reaction temperature is in the range between 200° C. and 450° C. and preferably between 250° C. and 350° C.

From a strict view point, it is impossible to operate a reaction step which produces only HCFC-124 or HFC-125. However, it is possible to produce HCFC-124 or HFC-125 of which amount is greater than that of the other by properly selecting reaction conditions such as a reaction temperature, catalyst to be used, a reaction time and so on, and particularly the reaction temperature. It is of course possible to produce the both compounds of the similar amounts. Generally, higher the reaction temperature is, the more amount of HFC-125 is produced. Thus, when HCFC-124 is to be produced, the reaction temperature is preferably reduced as much as possible. When HFC-125 is to be produced, the reaction temperature is preferably increased as much as possible. In addition, it is of course possible to produce HCFC-124 and HFC-125 as a mixture though the reaction within the above specified temperature range, and one of the compounds is finally obtained. Based on the concept of the present process, that is, the liquid phase first reaction and the vapor phase second reaction, those skilled in the art can easily select a separation process which separates HCFC-124 and/or HFC-125 from the second reaction mixture so as to finally obtain HCFC-124 and/or HFC-125.

The reaction time of the second reaction step, that is, a contact time with the catalyst (or an average residence time in the reaction step) is in the range usually between 0.5 to 60 seconds, and preferably between 2 and 10 seconds. An amount of HF per 1 mol of HCFC-123 and/or HCFC-122 is usually between 0.5 and 20 mol, and preferably between 1 and 9 mol. The feed supplied to the vapor phase reaction step, namely the reaction mixture obtained from the liquid phase reaction step optionally through the separation step as required, may contain other compounds such as HCFC-124 (in the case of the first aspect), trichlorofluoroethylene (which is hereinafter also referred to as "CFC-1111"), 1,1-dichlorodifluoroethylene (which is hereinafter also referred to as "CFC-1112a") in addition to HCFC-123 and/or HCFC-122 and HF.

The fluorination catalyst used in the vapor phase second reaction step is for example chromium (III) hydroxide, fluorinated chromium oxide produced by fluorinating with HF a thermally treated hydrate of chromium (III) hydroxide, fluorinated chromium oxide or fluorinated aluminum oxide formed by fluorinating chromium oxide or aluminum oxide with HF, aluminum fluoride, chromium fluoride, and alumina, partially fluorinated alumina or aluminum fluoride which carries at least one selected from Ti, V, Zr, Ge, Sn and Pb.

Fluorinated chromium oxide catalyst is preferably which is produced by partially fluorinating chromium oxide, particularly one having a specific surface area not less than 180 $m^2/g$, which catalyst is disclosed in Japanese Patent Kokai Publication (JP-A) No. 5-146680, the disclosure of which constitutes a part of the present description by the reference.

EFFECTS OF THE INVENTION

In the present process, PCE and HF are formed into HCFC-123 and/or HCFC-122 through the liquid phase reaction, and then HFC-125 in the first aspect or HCFC-124 in the second aspect is mainly formed through the vapor phase reaction of HCFC-123 and/or HCFC-122 with HF. The generation of heat is hardly observed in the vapor phase reaction step in which HFC-125 and/or HCFC-124 is formed from HCFC-123 and/or HCFC-122, and particularly in the vapor phase reaction step in which HCFC-123 is a main starting material. Thus, the stable temperature control is possible in the vapor phase reaction step of the present invention, and almost no hot spot is formed. Therefore, even an adiabatic reactor may be used in the vapor phase reaction step and a reactor cost is advantageously reduced.

In the vapor phase reaction step of HCFC-123 and/or HCFC-122 with HF, amounts of formed by-products are less than those of the prior art in which PCE and HF are reacted in the vapor phase, and a yield of HFC-125 is also better in the present invention. In addition, the reaction conditions of the vapor phase reaction step may be changed to a lower reaction temperature than that for the more HFC-125 production so that a greater amount of HCFC-124 may be produced. In the vapor phase reaction between PCE and HF in the prior art, the temperature control is difficult due to the exothermic reaction, and such vapor phase reaction is not preferable as a process of producing a larger amount of HCFC-124. To the contrary, an amount of generated reaction heat during the reaction between HCFC-123 and/or HCFC-122 and HF is extremely smaller than that in the case of the vapor phase reaction between PCE and HF so that the present invention has an advantage in that the temperature control is easy.

While the catalyst degradation is so remarkable in the prior art vapor phase reaction between PCE and HF that frequency of catalyst replacement or regeneration is disadvantageously increased, the catalyst degradation is relatively retarded in the vapor phase reaction between HCFC-123 and/or HCFC-122 and HF so that the frequency of the catalyst replacement or regeneration is reduced, which is advantageous in the view points of an operating efficiency and a catalyst cost.

When a cooling step is commercially used, water at around a room temperature is advantageously used as a cooling medium for the step from view points of an operation cost for obtaining the cooling medium and a facilities cost for a cooling system. Therefore, it is preferable to use cooling water at around a room temperature for cooling and liquefying a gas mixture into insoluble liquid phases or for condensation in a distillation step which separates a specific component. Then, it is cost-effective to use, in the present invention, boiling point increase of a material upon pressure increase of a system in which the material is present. That is, it is preferable in the present invention to operate, at a pressurized condition, various systems in which a mixture is present. For example, when a mixture which contains a compound having a low boiling point such as HCl, HFC-125 and/or HCFC-124 is subjected to a separation operation, it is usually preferable to operate such separation at a pressurized condition. For the pressurizing, a boosting means such as a booster or a compressor may be desirably used for the efficiency or simplification of the facilities.

When the reaction between PCE and HF is carried out in the vapor phase as in the prior art, PCE is easily liquified through the pressurization if unreacted PCE is still present in the reaction mixture, which makes it difficult to use a booster. Thus, in order to take out HFC-125 and/or HCFC-124 from the reaction mixture comprising PCE, HFC-125, HCFC-124, HCFC-123, HCl and HF, it is required to combine the steps of separation into the insoluble liquid phases and distillation. However, such combination is not economical since facilities for the combination are so complicated.

According to the present invention, the first reaction step is the liquid phase reaction, and substantially all PCE is present in the liquid phase (due to the higher boiling point). Thus, the first fraction which corresponds to the vapor phase equilibrating with the first reaction mixture (the liquid phase) obtained form the reaction step may be made hardly contain PCE. More preferably, such a vapor phase can be subjected to a distillation step having a single plate when a reflux condenser is equipped with a reactor of the liquid reaction, so that further separation of PCE can be carried out. Since from such first fraction, the second reaction mixture is obtained through the vapor phase second reaction step, also the second reaction mixture does not contain PCE, but contain mainly HFC-125, HCFC-124, HCFC-123, HCl and HF, which may be considerably easily pressurized using a booster.

For example, in the process for the production of HFC-125, the second reaction mixture may be separated into the three fractions through the pressurized distillation (i.e. the second (or the fifth) fraction, the third faction and the fourth fraction). The separation step may be carried out through a single distillation step conventionally used since HCFC-124 and HF, and HCFC-123 and HF form the azeotropes. Namely, the following fractions are formed: an overhead fraction comprising HCl and HFC-125 (corresponding to the third fraction), a side cut fraction comprising HCFC-124, HCFC-123 and a portion of HF which fraction is withdrawn from an intermediate tray (corresponding to the second fraction), and a bottom fraction comprising the rest of HF (corresponding to the fourth fraction). In one preferable embodiment, the fraction which is withdrawn from the intermediate tray and which comprises HF, HCFC-123 and HCFC-124 is recirculated to the vapor phase second reaction step, an objective product is separated from the overhead fraction, and the bottom fraction is preferably recirculated to the liquid phase first reaction step. Alternatively, the intermediate tray fraction and the bottom fraction are not separated, and all of them are recirculated to the second reaction step. Operation conditions which are generally used for the distillation operation like this include a pressure in the range between 1.0 MPa and 4.0 MPa (absolute pressure) and a reflux ratio in the range between about 1 and 5.

In the present process, the starting materials which are supplied from the outside of the process are PCE and HF. PCE is supplied to the liquid phase first reaction step. HF is directly supplied to the liquid phase first reaction step, and if necessary, HF may be additionally supplied from the outside to the feed to the vapor phase second reaction step, and/or supplied to the recirculated feed to the liquid phase first reaction step from the vapor phase second reaction step. The reason why HF is supplied directly to the vapor phase second reaction step or HF is additionally added from the outside to the fraction which is supplied to the vapor phase second reaction step is to properly adjust a molar ratio of HF/HCFC-123 (or a molar ratio of HF/(HCFC-123 and/or HCFC-122)) of the fraction introduced into the vapor phase second reaction step depending on the reaction conditions. When HF is added to the fraction supplied to the vapor phase second reaction stage, it is effective for the reaction that HF is added while it has been sufficiently preheated and mixed.

INDUSTRIAL APPLICABILITY

When HFC-125 and/or HCFC-124 are produced using PCE as a starting material, the degradation of the catalyst is suppressed, the reaction temperature control becomes easy, amounts of the by-products formed are reduced, so that HFC-125 and/or HCFC-124 can be efficiently and commercially produced.

DESCRIPTION OF PREFERABLE EMBODIMENTS

The first embodiment of the first aspect (the production process of HFC-125) of the present invention will be explained with reference to the process flow sheet shown in FIG. 1.

PCE and HF are supplied to the liquid phase reactor (11) (for example, at PCE/HF (mol %/mol %)=25/75), and reacted in the presence of the catalyst (for example $SbF_5$/$SbF_3$) at a reaction temperature in the range between 60° C. and 150° C. (for example 110° C.) and a reaction pressure in the range between 0.1 MPa and 3.0 MPa (absolute pressure) (for example 1.2 MPa-abs.) so as to produce the first reaction mixture which comprises HCFC-123 and/or HCFC-122. Using the separator (13) (for example, a distillation column or a reflux condenser), PCE and HF are recirculated to the liquid phase reactor (11) from the produced reaction mixture, and the first fraction which corresponds to the balance of the reaction mixture and which comprises the produced HCFC-123 and/or HCFC-122, HCl and HF, and preferably comprises the azeotropes+HCl, is supplied to the vapor phase reactor (12). As shown in FIG. 1, HF may be added to the reaction mixture at this stage which is to be supplied to the vapor phase reactor (12), if necessary. In the reactor (12), the second reaction mixture which comprises HFC-125 is formed in the presence of the catalyst (for example, $CrO_xF_y$) at a reaction temperature in the range between 250° C. and 450° C. (for example 320° C.) and a reaction pressure in the range between 0.1 MPa and 2.0 MPa (absolute pressure) (for example 0.2 MPa-abs.). Through the separator (15) (for example a distillation column), the produced second reaction mixture is separated into the second fraction comprising most of HCFC-123 and HCFC-124 of the second reaction mixture, the third fraction comprising most of HFC-125 and HCl of the second reaction mixture, and the fourth fraction comprising the balance of the second reaction mixture. When the distillation process is used for this separation, the third fraction is preferably obtained as the azeotropic mixture, and in such a case a portion of HF is entrained in the third fraction and the rest of HF occupies most of the fourth fraction.

As shown in FIG.1, the second fraction may be recirculated to the vapor phase second reaction step (12) together with the additional HF. At this stage, as shown in FIG. 1, HF may be added to the second fraction to be recirculated to the vapor phase second reaction step (12), if necessary. The third fraction is separated into HCl and HFC-125 as an objective compound through the separator (17) (for example, a distillation column) as shown in FIG. 1. The fourth fraction may be recirculated to the liquid phase first reaction step (11). Upon this recirculation, HF may be added to the fourth fraction which is to be recirculated to the liquid phase reactor (11) as shown in FIG. 1, if necessary. Further, the fourth fraction may be recirculated to the vapor phase reaction step, which is not shown. Alternatively, the second fraction and the fourth fraction may be separated together and for example, recirculated to the second reaction stage. When those conditions as described above are employed, a yield of HFC-125 is 97 to 99%.

The first embodiment of the second aspect can be generally carried out similarly to the above explanation except that the conditions of the vapor phase second reaction step are selected such that a more amount of HCFC-124 than that of the first aspect, and preferably substantially only HCFC-124 is produced (for example by lowering the reaction temperature to a temperature in the range for example between about 250° C. and 350° C.). In this case, although in fact, a small amount of HFC-125 may be produced, most of the produced HFC-125 is included in the third fraction. Thus, using the separator (15), following three fractions are separated: a fraction which mainly comprises HCFC-124 and a small amount of HFC-125 and HCl; a fraction which mainly comprises HCFC-123 and HF entrained therewith; and a fraction which mainly comprises HF. The fraction which mainly comprises HCFC-123 and HF is recirculated to the vapor phase reactor (12), and the fraction which mainly comprises HF is recirculated to the liquid phase reactor (11) and/or the vapor phase reactor (12). HCl is removed from the fraction which mainly comprises HCFC-124 and the small amount of HFC-125 and HCl through the separator (17) so that HFC-125 and HCFC-124 is obtained. These two compounds may be further divided into HFC-125 and HCFC-124 separately.

Next, the second preferable embodiment of the first aspect (the production process of HFC-125) of the present invention will be explained with reference in FIG. 2 which schematically shows the embodiment.

PCE and HF are supplied to the liquid phase first reaction step (21) (for example, at PCE/HF (mol %/ mol%)=25/75), and reacted in the presence of the catalyst (for example $SbF_5/SbF_3$) at a reaction temperature in the range between 60° C. and 150° C. and a reaction pressure in the range between 0.1 MPa and 3.0 MPa so as to produce HCFC-123 and/or HCFC-122. Using the separator (23) (for example, a reflux condenser), PCE and HF are recirculated to the liquid phase reactor (21) from the first reaction mixture produced, and simultaneously the first fraction is obtained. Further, using the separator (24), HCl is distilled off from the first fraction so as to obtain the fifth fraction. In this case, the first fraction may be pressurized using the booster (27) before supplying to the separator (24). The fifth fraction is supplied to the vapor phase second reaction step (22) (at this stage, HF may be added to the reaction mixture which is to be added to the vapor phase second reaction step (22)), and the fifth fraction is reacted in the presence of the catalyst (for example, $CrO_xF_y$) at a reaction temperature in the range between 250° C. and 450° C. to form HFC-125. The obtained second reaction mixture is separated into the three fractions using the separator (25): the second fraction which comprises most of HCFC-123 and/or HCFC-124 of the second reaction mixture and HF entrained therewith; the third fraction which comprises most of HFC-125 and HCl of the produced second reaction mixture; and the fourth fraction which comprised the rest of the HF. Upon the separation, the reaction mixture to be supplied to the separator (25) may be pressurized using the booster (26), if necessary. The second fraction is recirculated to the vapor phase second reaction step (22), the fourth fraction is recirculated to the liquid phase reactor (21) and/or the vapor phase reactor (22) (the latter recirculation is not shown), and HFC-125 is obtained from the third fraction by separating HFC-125 from HCl through the separator (28), for example a distillation column. Employing the conditions described as above, a yield of HFC-125 is 97 to 99%.

It is to noted that when HCFC-124 is produced, the conditions for the vapor phase second reaction step (22) are selected such that HCFC-124 is preferentially produced in the vapor phase second reaction step (22) and HFC-125 is hardly present in the second fraction. A small amount of HFC-125 may be formed. If it is the case, HFC-125 is present in the third fraction and behaves with HCFC-124. When an amount of HFC-125 is not acceptable, HFC-125 may be further separated from HCFC-124 after the separator (28), for example using distillation.

Further, the third preferable embodiment of the first aspect (the production process of HFC-125) of the present invention will be explained concretely with reference to FIG. 3 which schematically shows the embodiment.

PCE and HF are supplied to the liquid phase first reactor (31), and reacted in the presence of the catalyst (for example $SbF_5/SbF_3$) at a reaction temperature in the range between 60° C. and 150° C. and a reaction pressure in the range between 0.1 MPa and 3.0 MPa so as to produce HCFC-123 and/or HCFC-122 and obtain the first reaction mixture. Using the separator (33) (for example, a reflux condenser), PCE and a portion of HF which is entrained with PCE are recirculated to the liquid phase reactor (31) from the first reaction mixture produced, and simultaneously the rest of the first reaction mixture is obtained as the first fraction which comprises also HF and HCl. Further, after the first fraction is pressurized using the booster (37) if necessary, HCl is distilled off from the first fraction through the separator (34). The reaction mixture of which HCl has been removed through the separator (34) is obtained as the fifth fraction, which is supplied to the vapor phase second reaction step (32) (at this stage, HF may be added to the reaction mixture which is to be added to the vapor phase second reaction step (32)), and the fifth fraction is reacted in the presence of the catalyst (for example, $CrO_xF_y$) at a reaction temperature in the range between 250° C. and 450° C. to form a more amount of HFC-125 so that the second reaction mixture is obtained. The second reaction mixture is recirculated to the separator (34) such as a distillation column optionally after pressurizing with the booster (36). Through the separator (34), the following three fractions are formed: the third fraction which comprises most of HFC-125 and HCl of both the second reaction mixture; the second fraction which comprises most of HCFC-124 and HCFC-123 of both of the first fraction and the second reaction mixture and HF entrained therewith; and the fourth fraction which comprises the rest of the HF. The second fraction is supplied to the vapor phase reaction step (32) in place of the fifth fraction and reacted there, the fourth fraction is recirculated to the liquid phase first reaction step (31) and/or the vapor phase second reaction step (32) (the latter recirculation is not shown), and HFC-125 is obtained from the third fraction by separating HFC-125 from HCl through the separator (38), for example a distillation column. Employing the conditions described as above, a yield of HFC-125 is 97 to 99%.

It is to noted that when HCFC-124 is produced, the conditions for the vapor phase second reaction step (32) are selected such that HCFC-124 is preferentially produced in the vapor phase second reaction step (32) and HFC-125 is hardly present in the second fraction. A small amount of HFC-125 may be formed. If it is the case, HFC-125 is present in the third fraction and behaves with HCFC-124. When an amount of HFC-125 is not acceptable, HFC-125 may be additionally separated from HCFC-124 after the separator (38), for example using distillation.

Figure 2:
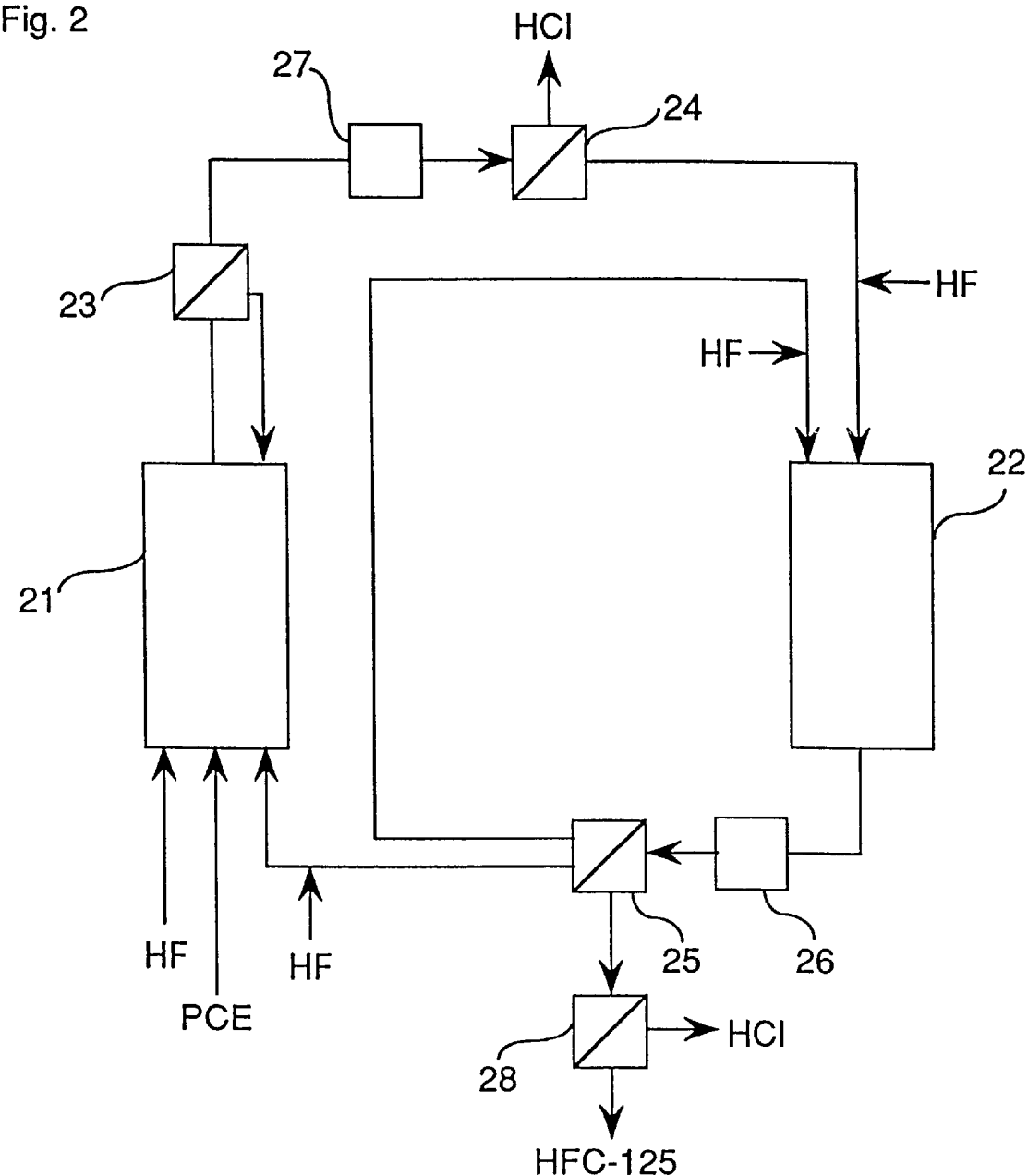
FIG. 2 is a process flow sheet which schematically shows a process of the second preferable embodiment of the first or the second aspect of the present invention.
Figure 3:
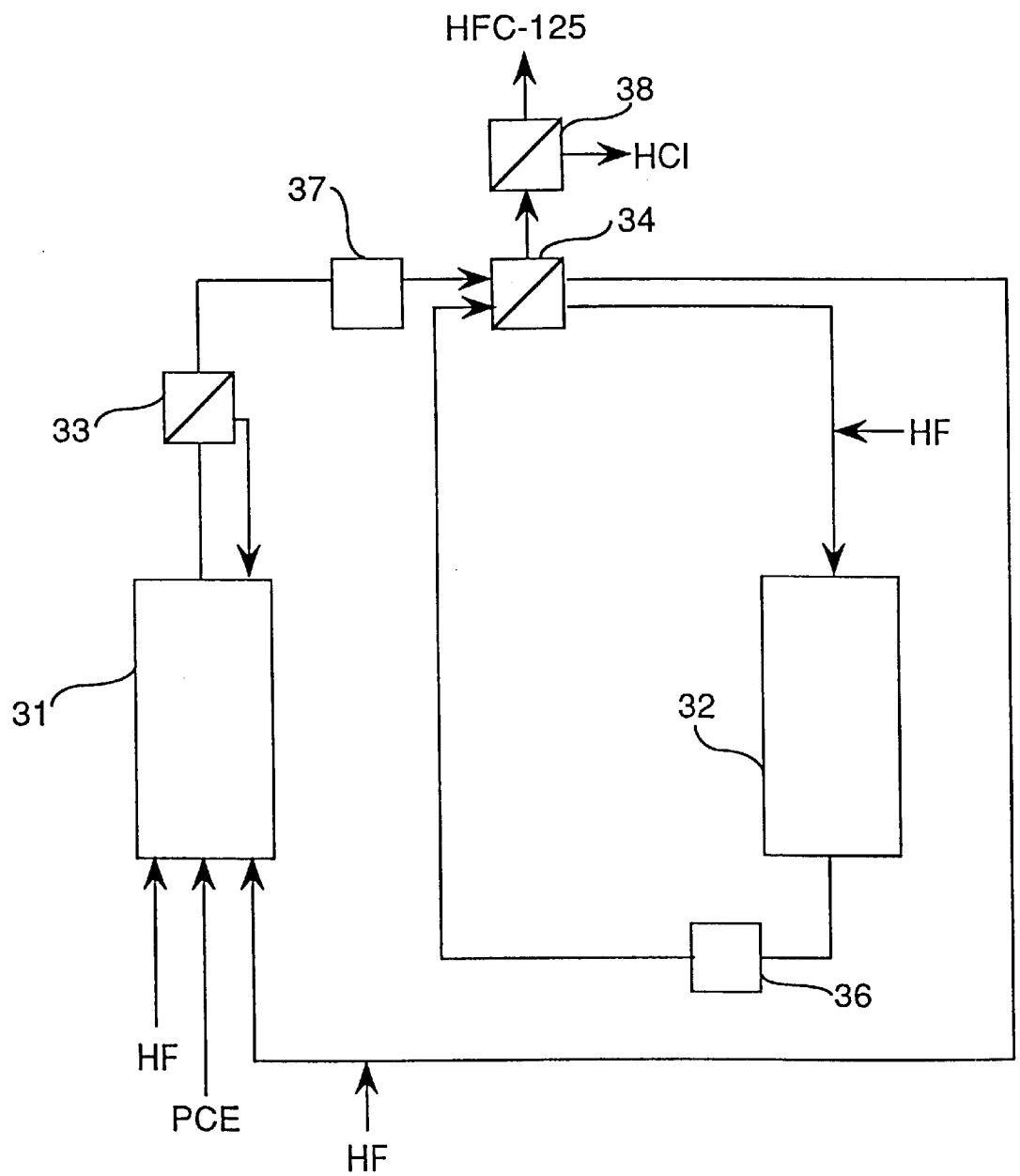
FIG. 3 is a process flow sheet which schematically shows a process of the third preferable embodiment of the first or the second aspect of the present invention.

The difference between the processes shown in FIGS. 2 and 3 is in that the process of FIG. 2 requires the four separators (23, 24, 25, and 27) while the process of FIG. 3 advantageously requires the three separators (33, 34 and 38). In the three embodiments, the vapor from an outlet of the vapor phase reaction step is divided into the three fractions, and the fraction which is to be recirculated to the liquid phase first reaction step and which comprises mainly HF may be divided and recirculated to the liquid phase first reaction step and/or the vapor phase second reaction step.

EXAMPLES

Example 1

Continuous fluorination of PCE was carried out in the liquid phase reaction (i.e. the first reaction step) using a 500 ml reactor (made of Hastelloy C) equipped with a reflux condenser at a reaction temperature 100° C. and a reaction pressure of 1.2 MPa (absolute pressure). In the fluorination, PCE and HF were continuously supplied to the reactor at a molar ratio of 1:3. The feed rate of PCE was 0.0026 mol/hr. The used catalyst was $SbF_3$ and $SbF_5$ at a molar ratio of 2:1 (totally 0.6 mol (113 g)).

Gas which was withdrawn from the reactor through the condenser and treated for acid removal was analyzed as to its composition of organic compounds using a gas chromatography (GC), the following results were obtained:

| | |
|---|---|
| HCFC-123: 94.7% by mol | HCFC-122: 1.3% by mol |
| HCFC-124: 0.3% by mol | CFC-1112a: 3.2% by mol |

Example 2

The vapor phase second reaction step was carried out using a tubular reactor (made of Hastelloy C, inner diameter: 25 mm) having a double-pipe heat exchanger. The reactor was filled with fluorination catalyst (fluorinated chromium oxide, 1500 g). HCFC-123, HF and HCl were supplied to the reactor heated to a temperature of 320° C. at feed rates of 5.62 (l/min.), 16.9 (l/min.) and 11.3 (l/min.) respectively and reacted (at a normal pressure) so as to form HFC-125. Gas from the reactor was treated for the acid removal and analyzed using GC. The gas had the following composition: HFC-125: 9.3% by mol, HCFC-124: 22.2% by mol, and HCFC-123: 68.5% by mol.

Temperature change was hardly observed in the reactor between before and after the supply of the reaction gases.

Example 3

As in Example 2, HCFC-123 and HF were supplied at flow rates of 5.62 (l/min.) and 16.9 (l/min.) respectively to the reactor which was heated to 320° C., and reacted so as to form HFC-125. Gas from the reactor was treated for the acid removal and analyzed using GC. The gas had the following composition: HFC-125: 30.4% by mol, HCFC-124: 28.6% by mol, and HCFC-123: 41.0% by mol.

Temperature change was hardly observed in the reactor between before and after the supply of the reaction gases.

Example 4

As in Example 2, HCFC-123 and HF were supplied at flow rates of 5.62 (l/min.) and 16.9 (l/min.) respectively to the reactor which was heated to 270° C., and reacted so as to form HCFC-124. Gas from the reactor was treated for the acid removal and analyzed using GC. The gas had the following composition: HFC-125: 1.11% by mol, HCFC-124: 14.72% by mol, and HCFC-123: 84.1% by mol.

Example 5

As in Example 1, continuous fluorination of PCE was carried out in a 300 liter reactor (made of Hastelloy C) equipped with a reflux condenser at a reaction temperature 100° C. and a reaction pressure of 1.2 MPa (absolute pressure). The used catalyst was $SbF_3$ and $SbF_5$ at a molar ratio of 2:1 (totally 300 mol). PCE (304 g/min.) and HF (184 g/min.) were continuously supplied to the reactor.

Gas withdrawn from the top of the condenser was introduced into and reacted in a vapor phase reactor (made of Hastelloy C, 30 liters) which was filled with fluorination catalyst (fluorinated chromium oxide, 25 kg). The reaction was carried out at a temperature of 320° C. (at a normal pressure). Produced gas from the vapor phase reactor was pressurized up to 1.6 MPa using a booster and then supplied to a fractionator so as to separate a fraction comprising HFC-125 and HCl from the top thereof.

In addition, the balance (HCFC-124, HCFC-123 and HF of which amount corresponds to the azeotropes with HCFC-124 and HCFC-123) was recirculated (i.e. returned) to an inlet of the vapor phase reactor and supply rates of PCE and HF to the liquid phase reactor were adjusted so that a still level of the fractionator was stabilized.

As a result, a composition of the feed at an inlet of the vapor phase reactor at the stabilized condition was as follows: HCFC-124: 5.5% by mol, HCFC-123: 21.3% by mol, HF: 55.4% by mol, and HCl: 17.5% by mol. An overall feed flow rate was 47.5 l/min at the inlet. A composition of the effluent from the vapor phase reactor was as follows: HFC-125: 8.7% by mol, HCFC-124: 5.5% by mol, HCFC-123: 12.6% by mol, HF: 37.9% by mol, and HCl: 34.9% by mol. An overall effluent flow rate was 47.5 l/min.

Comparative Example 1

Reaction was carried out using a tubular reactor (inner diameter: 25 mm) having a double-pipe heat exchanger. The reactor was filled with fluorination catalyst (fluorinated chromium oxide, 1500 g). PCE and HF were supplied to the reactor heated to a temperature of 350° C. at feed flow rates of 4.095 (l/min.) and 40.95 (l/min.) respectively and reacted so as to form HFC-125.

After the supply of the reaction gases, remarkable exothermic reaction was observed in which a temperature in the reactor was partially increased by about 10° C. Effluent gas from the reactor was treated for the acid removal and analyzed using GC. The gas had the following composition: HFC-125: 40.0% by mol, HCFC-124: 16.3% by mol, HCFC-123: 10.3% by mol, PCE: 28.6% by mol, and by-products (as impurities): 4.8% by mol.

The reaction was continued for 300 hours and the produced gas from the reactor was treated for the acid removal and analyzed as to its composition. The composition was as follows: HFC-125: 19.4% by mol, HCFC-124: 15.3% by mol, HCFC-123: 11.6% by mol, PCE: 46.3% by mol and by-products (as impurities): 7.4% by mol.

When compared with Example 6, hot spots were observed due to the heat of reaction.

Example 7

Reaction was carried out using a tubular reactor (made of Hastelloy C, inner diameter: 25 mm) having a double-pipe heat exchanger. The reactor was filled with fluorination catalyst (fluorinated chromium oxide, 1500 g). HCFC-123 and HF were supplied to the reactor heated to a temperature of 360° C. at feed flow rates of 4.28 (l/min.) and 25.3 (l/min.) respectively and reacted so as to form HFC-125. Gas from the reactor was treated for the acid removal and analyzed using GC. The gas had the following composition: HFC-125: 43.2% by mol, HCFC-124: 28.8% by mol, and HCFC-123: 28% by mol. The reaction was continued for 1400 hours, and gas from the reactor was treated for the acid removal and analyzed using GC. The gas had the following composition: HFC-125: 42.0% by mol, HCFC-124: 28.0% by mol, and HCFC-123: 30.0% by mol.

When compared with Comparative Example 1, no degradation tendency of the catalyst was hardly observed in the reaction from HCFC-123.

We claim:

1. A process of producing HCFC-124 comprising the steps of:

(2-ii-a) reacting PCE and HF in the presence of catalyst at a reaction temperature in the range between 60° C. and 150° C. in a liquid phase first reaction step so as to obtain a first reaction mixture comprising HCFC-123 and/or HCFC-122, (2-ii-b) obtaining a first fraction from the first reaction mixture which fraction comprises HCFC-123 and/or HCFC-122 and HCl and a portion of unreacted HF, (2-ii-c) obtaining a fifth fraction by removing HCl from the first fraction which contains HCl, (2-ii-d) reacting the fifth fraction, optionally with additional HF, in the presence of catalyst at a reaction temperature in the range between 200° C. and 450° C. in a vapor phase second reaction step so as to obtain a second reaction mixture comprising HCFC-123, HCFC-124, HCl and HF, (2-ii-e) separating the second reaction mixture into three fraction:
a second fraction which comprises most of HCFC-123 of the second reaction mixture and HF entrained therewith, a third fraction which comprises most of HCFC-124 and HCl of the second reaction mixture, and a fourth fraction which comprises the rest of HF, (2-ii-f) recirculating the second fraction to the step (2-ii-d) and reacting it together there, (2-ii-g) recirculating the fourth fraction to the step (2-ii-a) and/or the step (2-ii-d) and reacting it together there, and (2-ii-h) separating out, HCFC-124 from the third fraction.

2. The process according to claim 1 wherein the steps (2-ii-b) and (2-ii-c) are carried out in a single step.

3. The process according to claim 1 wherein in the step (2-ii-g), recirculating is carried out after HF is added to the fourth fraction.

4. The process according to claim 1 wherein in the step (2-ii-f), recirculating is carried out after HF is added to the second fraction.

5. The process according to claim 1 wherein the first fraction is pressurized between the steps (2-ii-b) and (2-ii-c), and/or the second reaction mixture is pressurized between the steps (2-ii-d) and (2-ii-e).

6. The process according to any one of claims 1 to 5 wherein the catalyst for fluorination in the vapor phase second reaction step is fluorinated chromium oxide prepared by treating chromium oxide as a base material so as to have a specific surface area of at least 180 $m^2/g$.

* * * * *